(12) United States Patent  (10) Patent No.: US 8,619,501 B2
Garcia-Osuna et al.  (45) Date of Patent: Dec. 31, 2013

(54) ULTRASONIC MEASUREMENTS PERFORMED ON ROCK CORES

(75) Inventors: Fernando Garcia-Osuna, Sugar Land, TX (US); Pierre Campanac, Sugar Land, TX (US)

(73) Assignee: Schlumberger Technology Corporation, Sugar Land, TX (US)

( * ) Notice: Subject to any disclaimer, the term of this patent is extended or adjusted under 35 U.S.C. 154(b) by 670 days.

(21) Appl. No.: 12/755,064

(22) Filed: Apr. 6, 2010

(65) Prior Publication Data

US 2011/0242938 A1    Oct. 6, 2011

(51) Int. Cl.
*G01V 1/00* (2006.01)
*G01V 11/00* (2006.01)

(52) U.S. Cl.
CPC ............. *G01V 1/00* (2013.01); *G01V 11/005* (2013.01)
USPC .......................................... 367/86; 73/152.11

(58) Field of Classification Search
USPC ......... 367/86, 89; 175/50, 60, 404; 73/152.11
See application file for complete search history.

(56) References Cited

U.S. PATENT DOCUMENTS

| 3,995,501 A | 12/1976 | Wiley |
| 4,466,495 A | 8/1984 | Jageler |
| 5,178,005 A * | 1/1993 | Peterson .................... 73/152.11 |
| 5,191,796 A * | 3/1993 | Kishi et al. ....................... 73/632 |
| 5,359,903 A | 11/1994 | Steiger et al. |
| 5,957,221 A | 9/1999 | Hay et al. |
| 6,006,844 A | 12/1999 | Van Puymbroeck et al. |
| 6,401,840 B1 | 6/2002 | Hay et al. |
| 6,585,045 B2 * | 7/2003 | Lee et al. .................... 166/252.5 |
| 6,641,434 B2 | 11/2003 | Boyle et al. |
| 6,788,066 B2 | 9/2004 | Wisler et al. |
| 6,941,231 B2 | 9/2005 | Zeroug et al. |
| 7,357,392 B1 * | 4/2008 | Wu ........................... 273/126 A |
| 7,500,388 B2 * | 3/2009 | Fujisawa et al. ............ 73/152.11 |
| 7,913,775 B2 * | 3/2011 | Jeffryes et al. ................... 175/58 |
| 2007/0137894 A1 | 6/2007 | Fujisawa et al. |
| 2009/0107724 A1 | 4/2009 | Utter et al. |

FOREIGN PATENT DOCUMENTS

WO    2006132861    12/2006

OTHER PUBLICATIONS

International Search Report and Written Opinion dated Sep. 27, 2011 for corresponding PCT Application No. PCT/US2011/031042 filed Apr. 4, 2011.

(Continued)

*Primary Examiner* — Luke Ratcliffe
*Assistant Examiner* — Krystine Breier
(74) *Attorney, Agent, or Firm* — Cathy Hewitt; John Vereb (57) ABSTRACT

One or more embodiments and methods of analyzing a formation sample with in a coring tool are disclosed herein. The methods and embodiments may include extracting a first core from a sidewall of a wellbore with a coring tool at a first depth, ultrasonically measuring a sound speed of the first core, transmitting the ultrasonically measured sound speed of the first core to a surface display unit, analyzing the ultrasonically measured sound speed in real time, determining the quality of the first core, extracting a second core at the first depth if the first core is determined to be low quality, and extracting the second core at a second depth if the core first is determined to be high quality.

19 Claims, 7 Drawing Sheets

(56) References Cited

OTHER PUBLICATIONS

Soucemarianadin, M. et al., Ultrasonic Saturation Mapping in Porous Media, SPE 16953, Dallas, TX, May 1989.

Gueguin, Y. et al., Cracks in Porous Rocks: Tiny Defects, Strong Effects, The Leading Edge, pp. 40-47, Jan. 2009.

Levedev, M. et al., Direct Laboratory Observation of Patchy Saturation and its Effects on Ultrasonic Velocities, The Leading Edge, pp. 24-27, Jan. 2009.

Hackert, C.L. et al., Estimating Scattering Attenuation from Vugs or Karsts, Geophysics, vol. 68, No. 4, pp. 1182-1188, Jul.-Aug. 2003.

* cited by examiner

ULTRASONIC MEASUREMENTS PERFORMED ON ROCK CORES

BACKGROUND OF THE DISCLOSURE

Wells are generally drilled into the ground or ocean bed to recover natural deposits of oil and gas, as well as other desirable materials that are trapped in geological formations in the Earth's crust. Wells are typically drilled using a drill bit attached to the lower end of a "drill string." Drilling fluid, or mud, is typically pumped down through the drill string to the drill bit. The drilling fluid lubricates and cools the bit, and may additionally carry drill cuttings from the borehole back to the surface.

In various oil and gas exploration operations, it may be beneficial to have information about the subsurface formations that are penetrated by a borehole. For example, certain formation evaluation schemes include measurement and analysis of the formation pressure and permeability. These measurements may be essential to predicting the production capacity and production lifetime of the subsurface formation.

Further, in addition to the formation testing tools, which may be primarily used to collect fluid samples, samples may also be taken of the formation rock within the borehole. For example, a coring tool may be used to take a core of the formation rock within the borehole. The typical coring tool usually includes a hollow drill bit, such as a coring bit, that is advanced into the formation wall such that a sample, such as a core, may be removed from the formation. Downhole coring operations generally include axial coring and sidewall coring. In axial coring, the coring tool may be disposed at the end of a drill string disposed within a borehole, in which the coring tool may be used to collect a core at the bottom of the borehole. In sidewall coring, the coring bit from the coring tool may extend radially from the coring tool, in which the coring tool may be used to collect a core from a side wall of the borehole.

As such, the core may then be transported to the Earth's surface, in which the sample may be analyzed to assess the porosity and the permeability of the material that makes up the formation surrounding the borehole, amongst other things such as the chemical and mineral composition of the fluids and mineral deposits contained in the pores of the formation and/or the irreducible water content contained in the formation. However, traditional coring tools may be limited in operation, such as by having limited storage area for cores, and further may not reliably break core samples away from the formation of the borehole.

BRIEF DESCRIPTION OF THE DRAWINGS

The present disclosure is best understood from the following detailed description when read with the accompanying figures. It is emphasized that, in accordance with the standard practice in the industry, various features are not drawn to scale. In fact, the dimensions of the various features may be arbitrarily increased or reduced for clarity of discussion.

DETAILED DESCRIPTION

It is to be understood that the following disclosure provides many different embodiments, or examples, for implementing different features of various embodiments. Specific examples of components and arrangements are described below to simplify the present disclosure. These are, of course, merely examples and are not intended to be limiting. In addition, the present disclosure may repeat reference numerals and/or letters in the various examples. This repetition is for the purpose of simplicity and clarity and does not in itself dictate a relationship between the various embodiments and/or configurations discussed. Moreover, the formation of a first feature over or on a second feature in the description that follows may include embodiments in which the first and second features are formed in direct contact, and may also include embodiments in which additional features may be formed interposing the first and second features, such that the first and second features may not be in direct contact.

Figure 1:
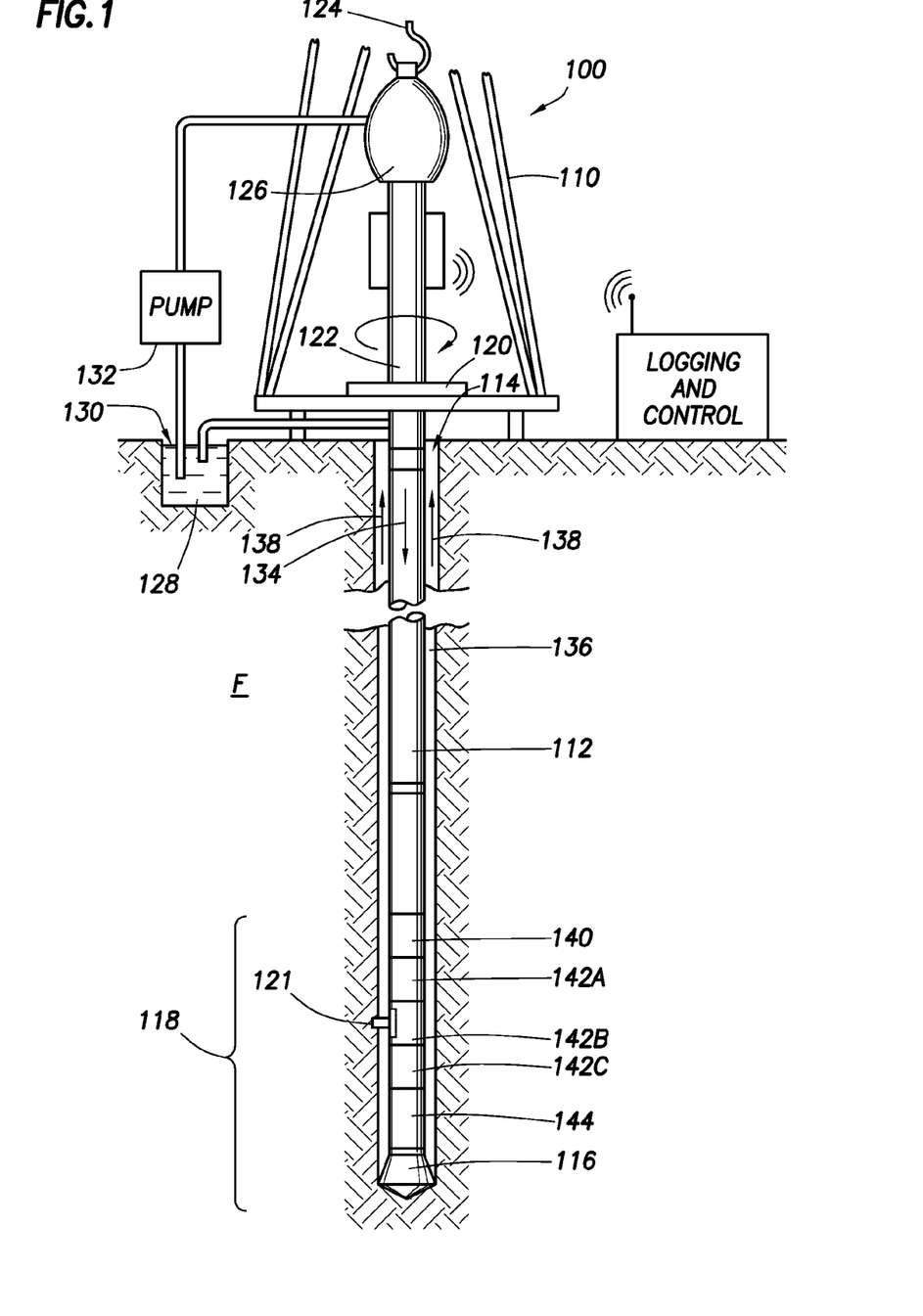
FIG. 1 shows a side view of a drilling and logging system in accordance with one or more embodiments of the present disclosure.

Referring now to FIG. 1, a side view of a drilling and logging system 100 having a drilling rig 110 with a drill string 112 suspended therefrom in accordance with one or more embodiments of the present disclosure is shown. The drilling and logging system 100 shown, or one similar thereto, may be used within onshore and/or offshore locations. In this embodiment, a borehole 114 may be formed within a subsurface formation F, such as by using rotary drilling, or any other method known in the art. As such, one or more embodiments in accordance with the present disclosure may be used within a wellsite, similar to the one as shown in FIG. 1 (discussed more below). Further, those having ordinary skill in the art will appreciate that the present disclosure may be used within other wellsites or drilling operations without departing from the scope of the present disclosure.

Continuing with FIG. 1, the drill string 112 may suspend from the drilling rig 110 into the borehole 114. The drill string 112 may include a bottom hole assembly 118 and a drill bit 116, in which the drill bit 116 may be disposed at an end of the drill string 112. The surface of the drilling and logging system 100 may have the drilling rig 110 positioned over the borehole 114, and the drilling rig 110 may include a rotary table 120, a kelly 122, a traveling block or hook 124, and may additionally include a rotary swivel 126. The rotary swivel 126 may be suspended from the drilling rig 110 through the hook 124, and the kelly 122 may be connected to the rotary swivel 126 such that the kelly 122 may rotate with respect to the rotary swivel.

Further, an upper end of the drill string 112 may be connected to the kelly 122, such as by threadingly connecting the drill string 112 to the kelly 122, and the rotary table 120 may rotate the kelly 122, thereby rotating the drill string 112 connected thereto. As such, the drill string 112 may be able to rotate with respect to the hook 124. Those having ordinary skill in the art, however, will appreciate that though a rotary drilling system is shown in FIG. 1, other drilling systems may be used without departing from the scope of the present disclosure. For example, a top-drive (also known as a "power swivel") system may be used in accordance with one or more embodiments without departing from the scope of the present disclosure. In such a top-drive system, the hook 124, swivel 126, and kelly 122 are replaced by a drive motor (electric or hydraulic) that may apply rotary torque and axial load directly to drill string 112.

The drilling and logging system 100 may further include drilling fluid 128 (also known as drilling "mud") stored in a pit 130. The pit 130 may be formed adjacent to the drilling and logging system 100, as shown, in which a pump 132 may be used to pump the drilling fluid 128 into the wellbore 114. In this embodiment, the pump 132 may pump and deliver the drilling fluid 128 into and through a port of the rotary swivel 126, thereby enabling the drilling fluid 128 to flow into and downwardly through the drill string 112, the flow of the drilling fluid 128 indicated generally by direction arrow 134. This drilling fluid 128 may then exit the drill string 112 through one or more ports disposed within and/or fluidly connected to the drill string 112. For example, in this embodiment, the drilling fluid 128 may exit the drill string 112 through one or more ports formed within the drill bit 116.

As such, the drilling fluid 128 may flow back upwardly through the borehole 114, such as through an annulus 136 formed between the exterior of the drill string 112 and the interior of the borehole 114, the flow of the drilling fluid 128 indicated generally by direction arrow 138. With the drilling fluid 128 following the flow pattern of direction arrows 134 and 138, the drilling fluid 128 may be able to lubricate the drill string 112 and the drill bit 116, and/or may be able to carry formation cuttings formed by the drill bit 116 (or formed by any other drilling components disposed within the borehole 114) back to the surface of the drilling and logging system 100. As such, this drilling fluid 128 may be filtered and cleaned and/or returned back to the pit 130 for recirculation within the borehole 114.

Though not shown in this embodiment, the drill string 112 may further include one or more stabilizing collars. A stabilizing collar may be disposed within and/or connected to the drill string 112, in which the stabilizing collar may be used to engage and apply a force against the wall of the borehole 114. This may enable the stabilizing collar to prevent the drill string 112 from deviating from the desired direction for the borehole 114. For example, during drilling, the drill string 112 may "wobble" within the borehole 114, thereby enabling the drill string 112 to deviate from the desired direction of the borehole 114. This wobble may also be detrimental to the drill string 112, components disposed therein, and the drill bit 116 connected thereto. However, a stabilizing collar may be used to minimize, if not overcome altogether, the wobble action of the drill string 112, thereby possibly increasing the efficiency of the drilling performed at the drilling and logging system 100 and/or increasing the overall life of the components at the drilling and logging system 100.

As discussed above, the drill string 112 may include a bottom hole assembly 118, such as by having the bottom hole assembly 118 disposed adjacent to the drill bit 116 within the drill string 112. The bottom hole assembly 118 may include one or more components therein, such as components to measure, process, and store information. Further, the bottom hole assembly 118 may include components to communicate and relay information to the surface of the wellsite.

As such, in this embodiment shown in FIG. 1, the bottom hole assembly 118 may include a tool string including one or more logging-while-drilling ("LWD") tools 142A, 142B, and 142C and/or one or more measuring-while-drilling ("MWD") tools 140. Further, the bottom hole assembly 118 may also include a steering-while-drilling system (e.g., a rotary-steerable system) and motor 144, in which the rotary-steerable system and motor 144 may be coupled to the drill bit 116.

The LWD tools 142A and 142B shown in FIG. 1 may include a thick-walled housing, commonly referred to as a drill collar, and may include one or more of a number of logging tools known in the art. Thus, the LWD tools 142A, 142B, and 142C may be capable of measuring, processing, and/or storing information therein, as well as capabilities for communicating with equipment disposed at the surface of the drilling and logging system 100. Further, those having ordinary skill in the art will appreciate that less than three LWD tools or more that three LWD tools be used within a tool string without departing from the scope of the present disclosure.

The MWD tool 140 may also include a housing (e.g., drill collar), and may include one or more of a number of measuring tools known in the art, such as tools used to measure characteristics of the drill string 112 and/or the drill bit 116. The MWD tool 140 may also include an apparatus for generating and distributing power within the bottom hole assembly 118. For example, a mud turbine generator powered by flowing drilling fluid therethrough may be disposed within the MWD tool 140. Alternatively, other power generating sources and/or power storing sources (e.g., a battery) may be disposed within the MWD tool 140 to provide power within the bottom hole assembly 118. Further, the MWD tool 140 may include one or more of the following measuring tools: a weight-on-bit measuring device, a torque measuring device, a vibration measuring device, a shock measuring device, a stick slip measuring device, a direction measuring device, an inclination measuring device, a natural gamma ray measuring device, and/or any other device known in the art used within an MWD tool.

The LWD tools 142A, 142B and 142C may include one or more formation evaluation or sampling tools. As such, the LWD tools may include sensors (not shown) for taking geophysical measurements. As shown, a sidewall coring tool 121 may be disposed within the bottom hole assembly 118 such as within the LWD tool 142B. The sidewall coring tool 121 may be used to acquire samples of the formation F, such as coring samples. The LWD tool 142B may also permit performing downhole ultrasonic measurements on sidewall coring samples according to one or more embodiments of the present disclosure.

Figure 2:
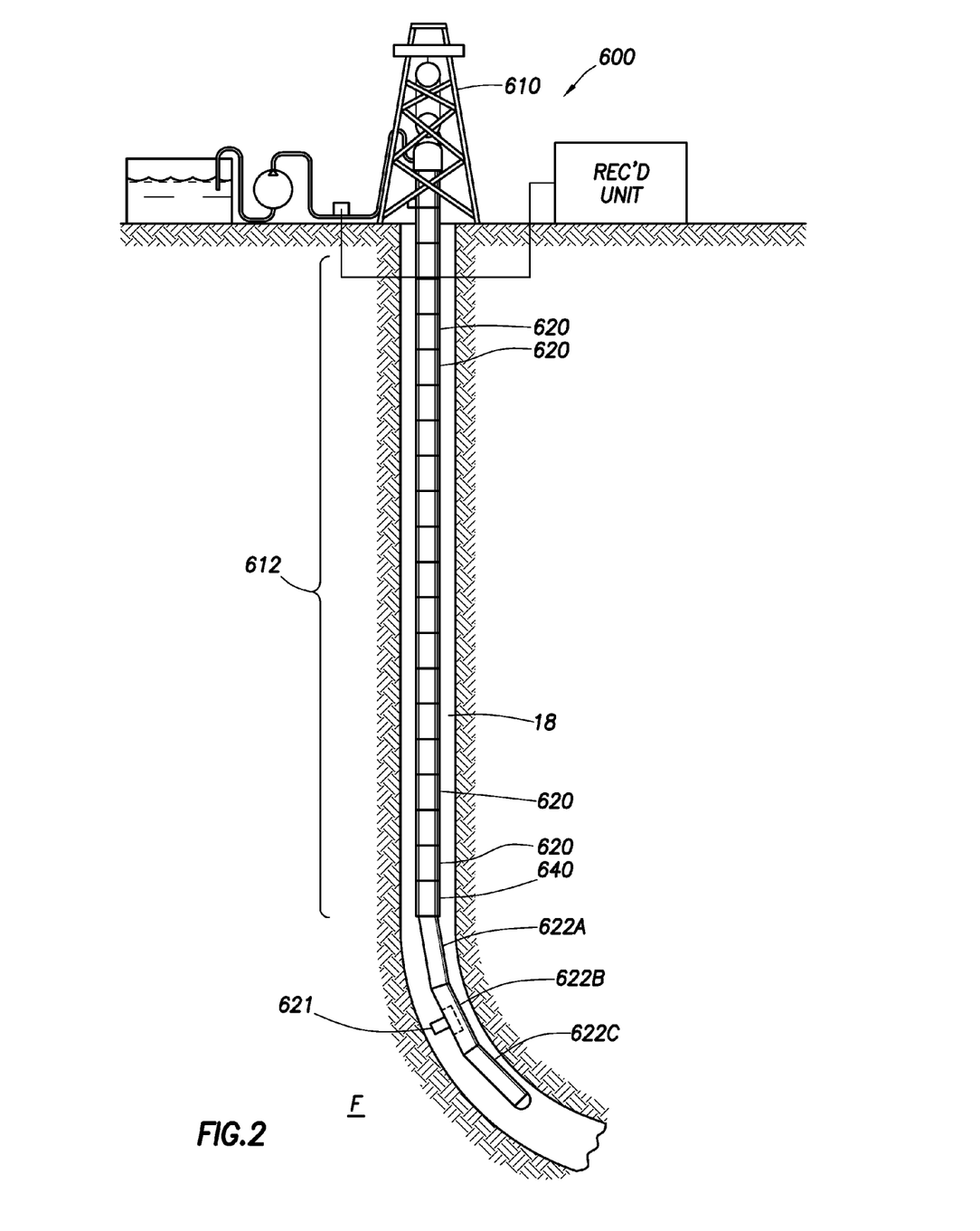
FIG. 2 shows a side view of a logging system in accordance with one or more embodiments of the present disclosure.

Referring now to FIG. 2, a side view of a logging system 600 having a drilling rig 610 in accordance with one or more embodiments of the present disclosure is shown. In this embodiment, a borehole 614 may be formed within a subsurface formation F, such as by using a drilling assembly, or any other method known in the art. Further, in this embodiment, a wired pipe string 612 may be suspended from the drilling rig 610. The wired pipe string 612 may be extended into the borehole 614 by threadably coupling multiple segments 620 (i.e., joints) of wired drill pipe together in an end-to-end fashion. As such, the wired drill pipe segments 620 may be similar to that as described within U.S. Pat. No. 6,641,434, filed on May 31, 2002, entitled "Wired Pipe Joint with Current-Loop Inductive Couplers," and incorporated herein by reference.

Wired drill pipe may be structurally similar to that of typical drill pipe, however the wired drill pipe may additionally include a cable installed therein to enable communication through the wired drill pipe. The cable installed within the wired drill pipe may be any type of cable capable of transmitting data and/or signals therethrough, such an electrically conductive wire, a coaxial cable, an optical fiber cable, and or any other cable known in the art. Further, the wired drill pipe may include having a form of signal coupling, such as having inductive coupling, to communicate data and/or signals between adjacent pipe segments assembled together.

As such, the wired pipe string 612 may include a tool string including one or more tools 622A, 622B and 622C and/or instruments disposed within the pipe string 612. For example, as shown in FIG. 2, a string of multiple borehole tools 622A, 622B and 622C may be coupled to a lower end of the wired pipe string 612. Further, those having ordinary skill in the art will appreciate that less than three tools or more that three tools be used within a tool string without departing from the scope of the present disclosure.

The tools 622A, 622B and 622C may be connected to the wired pipe string 612 during drilling the borehole 614, or, if desired, the tools 622A, 622B and 622C may be installed after drilling the borehole 614. If installed after drilling the borehole 614, the wired pipe string 612 may be brought to the surface to install the tools 622A, 622B and 622C, or, alternatively, the tools 622A, 622B and 622C may be connected or positioned within the wired pipe string 612 using other methods, such as by pumping or otherwise moving the tools 622A, 622B and 622C down the wired pipe string 612 while still within the borehole 614. The tools 622A, 622B and 622C may then be positioned within the borehole 614, as desired, through the selective movement of the wired pipe string 612, in which the tools 622 may gather measurements and data. These measurements and data from the tools 622A, 622B and 622C may then be transmitted to the surface of the borehole 614 using the cable within the wired drill pipe 612.

A power sub 640 may tool 140 may include an apparatus for generating and distributing power within the tools 622A, 622B and/or 622C. For example, a mud turbine generator powered by flowing drilling fluid therethrough may be disposed within the power sub 640. Alternatively, other power generating sources and/or power storing sources (e.g., a battery) may be disposed within the power sub 640 to provide power within the tools 622A, 622B and/or 622C. Further, the power sub 640 may include one or more of the following measuring tools: a weight-on-bit measuring device, a torque measuring device, a vibration measuring device, a shock measuring device, a stick slip measuring device, a direction measuring device, an inclination measuring device, a natural gamma ray measuring device, and/or any other device known in the art used within an MWD tool.

The tools 622A, 622B and 622C may include one or more tools used within wireline applications, may include one or more LWD tools, may include one or more formation evaluation or sampling tools, and/or may include any other tools capable of measuring a characteristic of the formation F. As shown, a sidewall coring tool 621 may be disposed, for example, within the tool 622B. The sidewall coring tool 621 may be used to acquire samples of the formation F, such as coring samples. The tool 622B may also permit performing downhole ultrasonic measurements on sidewall coring samples according to one or more embodiments of the present disclosure.

Figure 3:
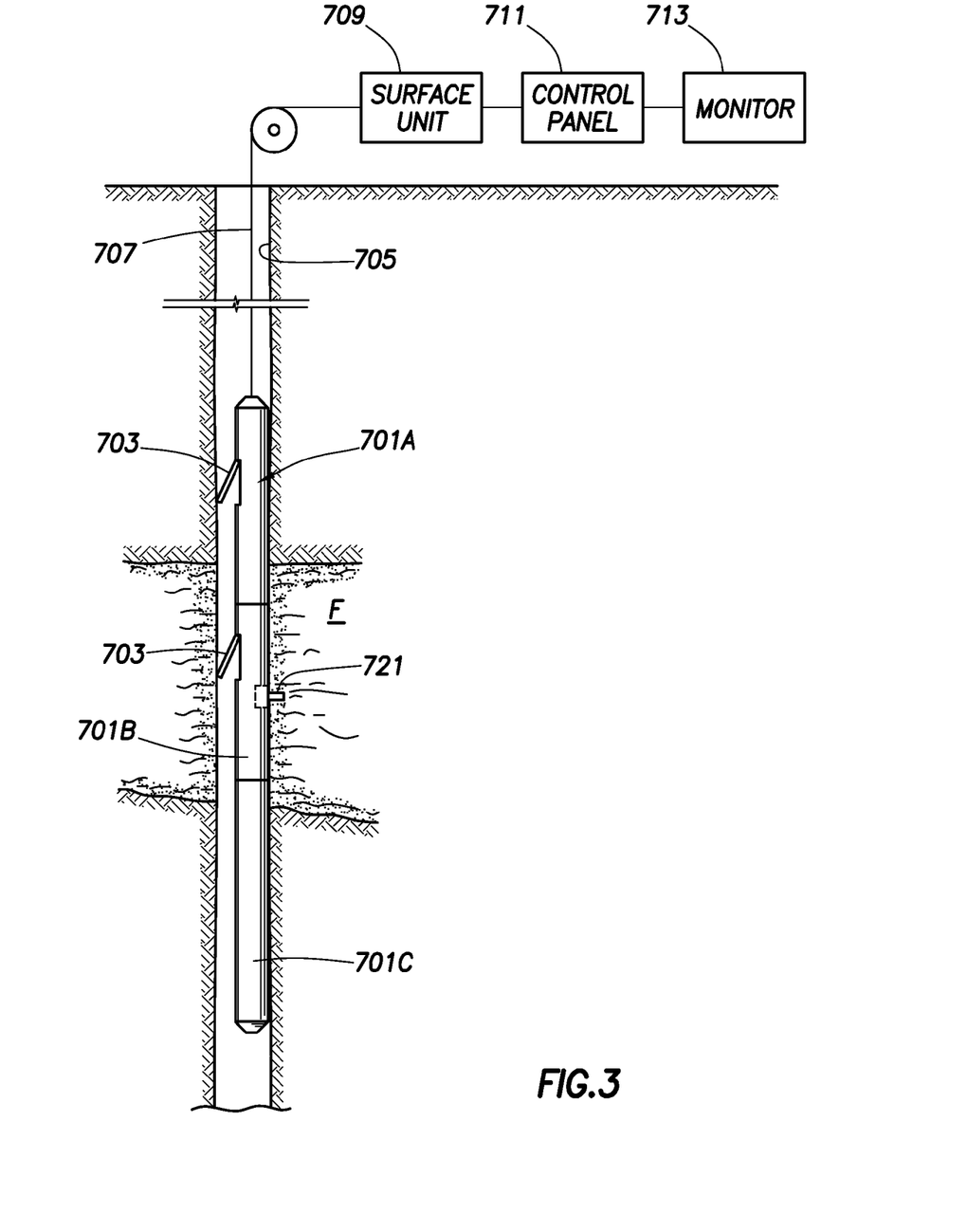
FIG. 3 shows a side view of a wireline logging system in accordance with one or more embodiments of the present disclosure.

Referring now to FIG. 3, a side view of a wireline logging system in accordance with one or more embodiments of the present disclosure is shown. A wireline tool string may include one or more tool such as, for example, the wireline tools 701A, 701B and 701 C. In this embodiment, the wireline tools 701A, 701B and 701 C may be suspended within a borehole 705 formed within a subsurface formation F, in which the wireline tools 701A, 701B and 701 C may be suspended from an end of a multi-conductor cable 707 located at the surface of the formation F. Further, those having ordinary skill in the art will appreciate that less than three tools or more that three tools be used within a tool string without departing from the scope of the present disclosure.

The wireline tools 701A, 701B and 701 C may also include other formation evaluation tools (not shown) having sensors for taking geophysical measurements, as well as other general purpose tools having a tension compression measuring device, a temperature measuring device, a vibration measuring device, a shock measuring device, a direction measuring device, an inclination measuring device, and/or any other device known in the art or future-developed.

As shown, a coring tool 721 may be disposed within an elongate housing of the wireline tool 701B such that the coring tool 721 may be disposed downhole within the borehole 705. As shown, the tool string 701A, 701B, 701C may include one or more pistons 703 (e.g., anchoring shoes) that may be able to extend from the housing of the tool string 701 and engage the wall of the borehole 705. As such, this may enable the pistons 703 to provide stability to the tool string 701 and coring tool 721, particularly when the coring tool 721 is drilling into the formation F.

As such, the cable 707 may enable the wireline tool 701B and the coring tool 721 to be electrically coupled to a surface unit 709, in which the surface unit 709 may further include a control panel 711 and/or a monitor 713. The surface unit 709 may be able to provide electrical power to the coring tool 721, such as to monitor the status of the downhole coring and other activities of downhole equipment with the tool string 701, in addition to being able to control the activities of the coring tool 721 and other downhole equipment with the wireline tools 701A, 701B and 701 C. Further, the coring tool 721 may include one or more electric motors that may be powered, for example, through the use of the power provided from the cable 707. Although the embodiments shown in FIG. 3 show the cable 707 used to provide power to the coring tool 721, those having ordinary skill in the art will appreciate that other methods may be used to provide power to a coring tool, such as by the use of a battery, a power cell, and/or an electrically charged accumulator disposed downhole.

The sidewall coring tool 721 may be used to acquire samples of the formation F, such as coring samples. The tool 701B may also permit performing downhole ultrasonic measurements on sidewall coring samples according to one or more embodiments of the present disclosure.

Figure 4A:
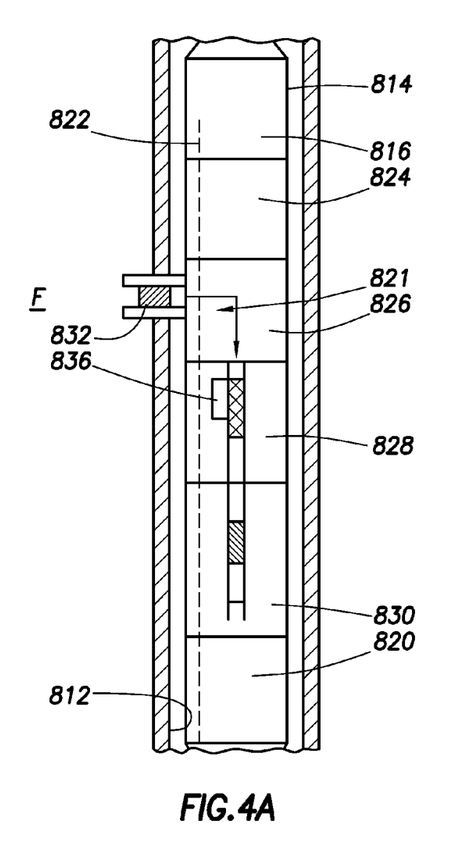
FIG. 4A shows a schematic view of a tool string having a coring tool in accordance with one or more embodiments of the present disclosure.

Referring now to FIG. 4A, a schematic view of a tool string 814 in accordance with embodiments disclosed herein is shown. As such, the tool string 814 and one or more methods of using the tool string 814 in accordance with the present disclosure, may be included within one or more of the embodiments shown in FIGS. 1-3, in addition to being included within other tools and/or devices that may be disposed downhole within a formation. For example, the tool string 814 may be used to implement part of all the LWD tools 142A, 142B and 142C shown in FIG. 1, the downhole tools 622A, 622B, and 622C shown in FIG. 2 and/or the wireline tools 701A, 702, and 703C shown in FIG. 3.

As shown, a sidewall coring tool 821 may be one component disposed on the tool string 814 having several additional tools 816, 820 disposed above and/or below sidewall coring tool 821. In certain embodiments, measurement units disposed in, for example, sidewall coring tool 821, may be connected to a tool bus 822 and a telemetry unit 824. Telemetry means may connect telemetry unit 824 to a data acquisition and processing apparatus disposed above at the Earth' surface above the borehole 812. As such, telemetry means may allow the transfer of a signal from the measurement units to data acquisition and processing apparatus where the data may be displayed in real time.

Still referring to FIG. 4A, the sidewall coring tool 802 may include a mechanical coring section 826, a core analysis section 828, and a core storage section 830. Mechanical coring section 826 may extract core sample 832 from a formation F at a driller depth measured along the borehole 812. Mechanical coring section 826 may then convey the extracted core sample 832 to core analysis section 828 where a measurement unit 836 may determine a quality of core sample 832. Measurement unit 836 may be connected to telemetry unit 824 by tool bus 822 such that data collected by measurement unit 836 may be transmitted to data acquisition and processing apparatus.

Figure 4B:
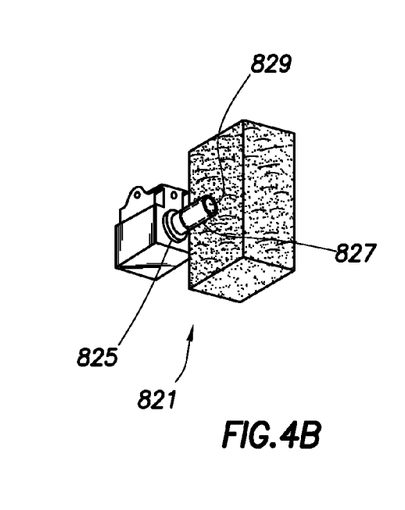
FIG. 4B shows a perspective view of a coring tool in accordance with one or more embodiments of the present disclosure.

FIG. 4B shows a perspective view of the coring tool 821. Referring to FIGS. 4A and 4B, the coring tool 821 is shown in the coring position, in which the coring tool 821 is used to drill into the wall of a borehole 812 and receive a core. The coring tool 821 may include a coring bit 827, in which the coring bit may have an open end 829 for cutting into the formation F and receiving a core 832. Further, the coring tool 821 may be able to extend and retract the coring bit into and out of the coring tool 821, and may also be able to rotate the coring bit against the wall of the borehole 812. For example, one motor may be used to rotate and apply torque to the coring bit, and the other may be used to extend/retract and apply weight on the coring bit.

As such, the coring bit 827 may be rotated by a motor 825, in which the coring bit 827 receives the core 832 into the coring bit 827 through the open end 829. The coring bit 827 may then be retracted within the mechanical coring section 826, in which the core may be stored within a storage area 830 of the tool string 814.

As such, a coring tool, and one or more methods of using a coring tool, in accordance with the present disclosure may be included within one or more of the embodiments shown in FIGS. 1-4B, in addition to being included within other tools and/or devices that may be disposed downhole within a formation. The coring tool, thus, may be used to extract one or more cores from the borehole of a formation. As shown in the FIGS. 1-4B, only a sidewall coring tool is shown. However, those having ordinary skill in the art will appreciate that other coring tools may also be included within one or more embodiments without departing from the scope of the present disclosure. A such, the coring tool may be an axial coring tool and/or a sidewall coring tool, in which the coring tool includes a coring bit that may be used to extract a core from the wall of the borehole.

A coring tool in accordance with one or more embodiments of the present disclosure may include, at least, a coring bit movably attached to the coring tool. For example, the coring bit may be able to extend and retract from the coring tool such that the coring bit may be able to be received within a wall of a borehole. Further, the coring bit may be able to rotate with respect to the coring tool, such as when the coring bit is extended from the coring tool. This may enable the coring bit to drill into and collect a core from the wall of the borehole when disposed downhole. Furthermore, the coring bit may be able to move with respect to the coring tool, such as by having the coring bit move between positions when disposed within the coring tool. For example, the coring bit may further be able to move between a coring position and an ejection position within the coring tool.

The coring tool may further include an ejector rod disposed therein, in which the ejector rod may also be movably disposed within the coring tool. For example, the ejector rod may be able to move between multiple positions, such as move between a retracted position and an extended position. When moving between positions, the coring bit may be disposed within the ejection position. As such, the ejector rod may be able to move from the retracted position, through the coring bit, and into an extended position.

Such movement of the ejector rod may enable the ejector rod to determine the presence and/or length of a core if a core has been successfully drilled from a borehole wall and received into the coring tool with the coring bit. For example, as the ejector rod moves through the coring bit, the ejector rod may push a core out of the coring bit, if such a core is present within the coring bit of the coring tool. The ejector rod may then push the core into a core holder, for example, disposed within the coring tool. As the ejector rod moves through the coring bit and into an extended position, the ejector rod may then engage the top of the core, if such a core is present within the coring tool, or the ejector rod may engage the inner bottom of the core holder, if such a core is not present within the coring tool.

As such, the distance of the movement of the ejector rod between the retracted position and the extended position may be measured. Such a measurement of the distance of movement of the ejector rod may then enable the presence, length, and/or other measurements or properties of a core to be determined. As such, the present disclosure contemplates one or more methods to drill within a borehole with a coring tool and/or one or more methods to detect the presence and/or determine the length of a core within a coring tool.

Figure 5:
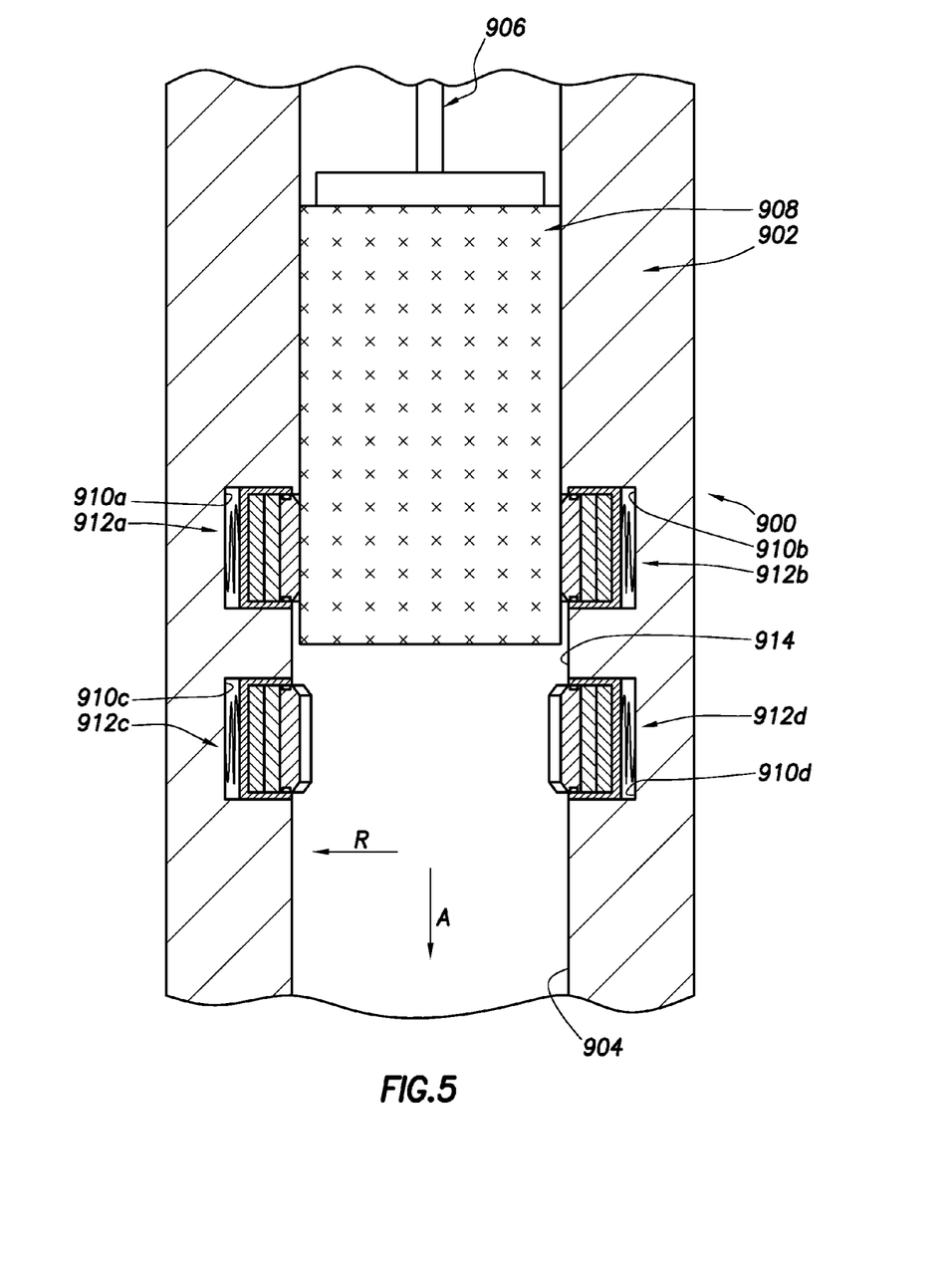
FIG. 5 shows a partial cross sectional view of an analysis section of a sidewall coring tool in accordance with one or more embodiments of the present disclosure.

Referring now to FIG. 5, a partial cross-sectional view of a core analysis section 900 in accordance with embodiments disclosed herein is shown. Core analysis section 900 may include a body 902 having a passageway 904 extending axially therethrough. An ejector rod 906 may be configured to push a core 908 through passageway 904. In certain embodiments, core 908 may be approximately one inch in diameter and approximately three inches in length; however, those having ordinary skill in the art will appreciate that other sizes of core 908 may also be used.

One or more of cavities 910a, 910b, 910c, 910d may be disposed in diametrically opposed pairs on an inner surface 914 of body 902. For example, a first cavity 910a may be diametrically opposed from a second cavity 910b, thereby forming a first pair of cavities, and a third cavity 910c may be diametrically opposed from a fourth cavity 910d, thereby forming a second pair of cavities. The multiple pairs of cavities may be disposed on inner surface 914 of body 902. One or more of the cavities 910a, 910b, 910c, 910d may include a corresponding ultrasonic measurement unit assembly 912a, 912b, 912c, 912d disposed therein, such that the ultrasonic measurement unit assemblies are positioned in diametrically opposed pairs.

Figure 6:
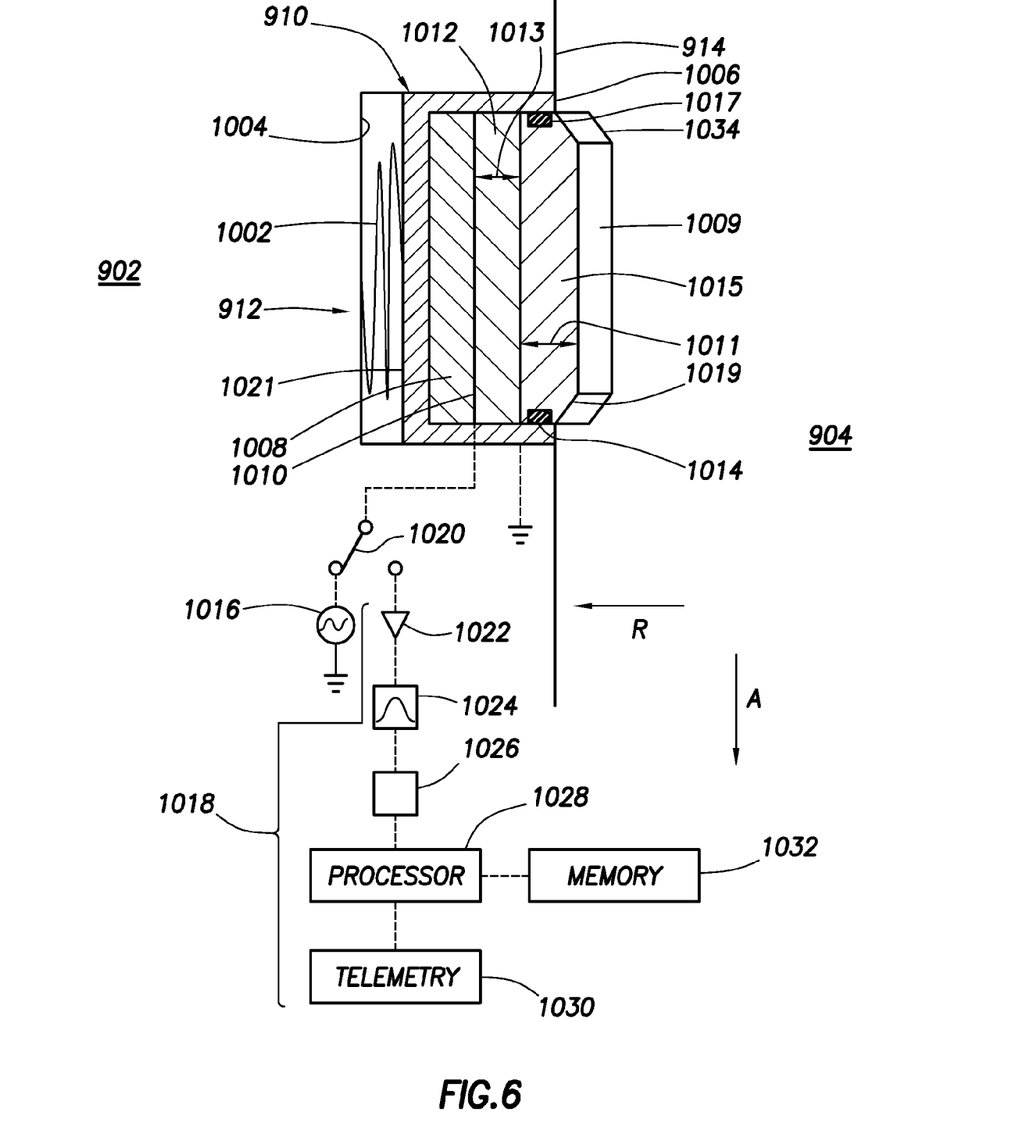
FIG. 6 shows a cross sectional view of an ultrasonic measurement unit assembly in accordance with one or more embodiments of the present disclosure.

Referring now to FIG. 6, a cross-sectional view of an ultrasonic measurement unit assembly 912 in accordance with embodiments disclosed herein is shown. Ultrasonic measurement unit assembly 912 may be disposed in cavity 910 on inner surface 914 of core analysis section 900, as discussed above. A compressible coupling 1002 such as, for example, a spring or a Belleville washer, may connect a back surface 1021 of an insulating body 1006 to a longitudinal surface 1004 of cavity 910 such that relative radial motion between longitudinal surface 1004 of cavity 910 and ultrasonic measurement unit assembly 912 may be allowed.

When compressible coupling 1002 is not in compression, an inner contact surface 1009 of a cover plate 1015 may extend past inner surface 914 of body 902 into passageway 904. Cover plate 1015 may be configured to receive a core (not shown) and may include a beveled top edge 1034 and an arcuate inner contact surface 1009 having a curve configured to contact part of an outer surface of the core. Beveled top edge 1034 may allow the core to slide between two initially uncompressed ultrasonic measurement unit assemblies and further axial movement of the core by ejector rod 906 may radially compress the ultrasonic measurement unit assemblies 912a, 912b, as shown in FIG. 5.

In such an embodiment, the arcuate inner contact surface 1009 may provide for increased contact area between cover plate 1015 and a core surface, thereby allowing effective transmission of waves from a transmitter and efficient reception of waves by a receiver. Additionally, in certain embodiments, the compressibility of compressible coupling 1002 may be selected such that a relatively low contact pressure may be applied to the core by cover plate 1015. A lower contact pressure between the core and cover plate 1015 may reduce the likelihood of damaging the core.

Additionally, each ultrasonic measurement unit assembly 912 may be configured as a transmitter, a receiver, or both. For example, ultrasonic measurement unit assembly 912 may include a piezoelectric ceramic 1012 plated with a first electrode 1010 and a second electrode 1014. First electrode 1010 may be disposed on a first surface of piezoelectric ceramic 1012 and second electrode 1014 may be disposed on a second surface of piezoelectric ceramic 1012, in which the first surface may be opposite the second surface.

To act as a transmitter, first electrode 1010 may be connected to a pulse generator 1016 and second electrode 1014 may be grounded. Pulse generator 1016 may send short and wideband pulses to piezoelectric ceramic 1012 through first electrode 1010. Piezoelectric ceramic 1012 may be polarized to transmit different types of ultrasonic waves. For example, piezoelectric ceramic 1012 may be polarized in an axial direction, A, or in a radial direction, R. A piezoelectric ceramic 1012 polarized in axial direction A may be used to transmit a shear wave, or an S-wave, through the core (not shown). In an S-wave, particles of the core may oscillate in a direction perpendicular to the direction in which the wave propagates. A piezoelectric ceramic 1012 polarized in radial direction R may be used to transmit a compressional wave, or a P-wave, through the core. In a P-wave, particles may oscillate in the direction of wave propagation.

In certain embodiments, the short and wideband pulses from pulse generator 1016 may be calibrated to a central driving frequency of approximately 0.5 megahertz (MHz) for S-waves and approximately 1.0 MHz for P-waves. A thickness 1013 of piezoelectric ceramic 1012 may be selected such that the piezoelectric ceramic 1012 resonates at a desired central driving frequency. Additionally, in one embodiment, cover plate 1015 may be designed having a thickness 1011 approximately one-quarter of the wavelength of the S-wave or P-wave in cover plate 1015. For example, in certain embodiments having an aluminum cover plate 1015, cover plate thickness 1011 may be between approximately 0.05 inches (1.2 mm) and approximately 0.06 inches (1.5 mm).

Alternatively, ultrasonic measurement unit assembly 912 may act as a receiver. In such an embodiment, first electrode 1010 may be connected to a receiver assembly 1018 and second electrode 1014 may be grounded. Receiver assembly 1018 may include a preamplifier 1022 to prepare a received ultrasonic signal for further processing, an anti-aliasing filter 1024 to restrict the bandwidth of the ultrasonic signal, and an analog-to-digital converter 1026 for converting a continuous ultrasonic signal to a discrete digital signal. The digital signal may then be processed by processor 1028, stored in memory 1032, and/or transmitted by telemetry package 1030. In certain embodiments, a digital signal may be transmitted via a wired or wireless telemetry package 1030 to a surface unit for display and analysis. Those of ordinary skill in the art will appreciate that in certain embodiments, the digital signal may be transmitted to a surface unit in raw form for processing and analysis.

In certain embodiments, ultrasonic measurement unit assembly 912 may include an electrical switch 1020 configured to connect to a pulse generator 1016 or a receiver assembly 1018. As such, an ultrasonic wave may be transmitted by ultrasonic measurement unit assembly 912 when ultrasonic measurement unit assembly 912 is connected to pulse generator 1016. The ultrasonic wave may propagate through the core, reflect, and travel back through the core toward ultrasonic measurement unit assembly 912. Switch 1012 may then be moved to connect ultrasonic measurement unit assembly 912 with receiver assembly 1018 such that ultrasonic measurement unit assembly 912 may receive the reflected ultrasonic wave. Thus, a single ultrasonic measurement unit assembly 912 may act as both a transmitter and a receiver.

Referring back to FIG. 5, a first ultrasonic measurement unit assembly 912a configured as a transmitter and a second ultrasonic measurement unit assembly 912b configured as a receiver are shown in contact with core 908. As discussed above, first ultrasonic measurement unit assembly 912a may be disposed diametrically opposite second ultrasonic measurement unit assembly 912b. In such an embodiment, ultrasonic waves may be repeatedly transmitted by first ultrasonic measurement unit assembly 912a and may propagate through a cross section of core 908. The ultrasonic waves may then be received and measured by second ultrasonic measurement unit assembly 912b and a time of flight of the ultrasonic wave traversing core 908 may be measured. Although ultrasonic measurement unit assemblies 912a, 912b, 912c, 912d are shown in FIG. 5 in diametrically opposed, axially aligned pairs, other placements of the ultrasonic measurement unit assemblies may be used. For example, ultrasonic measurement unit assemblies may be provided in the direction perpendicular to the sectional plane shown in FIG. 5, thereby providing for a plurality of ultrasonic wave measurements across different diameters of core 908.

In certain embodiments, transmission and reception of ultrasonic waves by ultrasonic measurement unit assemblies 912a, 912b may occur as core 908 is pushed at a continuous speed by ejector rod 906. In other embodiments, ejector rod 906 may momentarily stop at several position intervals while ultrasonic wave transmission and reception is performed by ultrasonic measurement unit assemblies 912a, 912b, respectively, thereby reducing the amount of friction noise that may be received by ultrasonic measurement unit assembly 912b.

Ultrasonic waves received by ultrasonic measurement unit assemblies may be indicative of core quality. To determine characteristics of the ultrasonic waves, a wave profile may be compiled by indexing received ultrasonic waves with a position of core 908. Ejector rod 906 may include a measurement device such as, for example, a linear potentiometer, operatively coupled thereto that may store or relay position information. Because core 908 is pushed by ejector rod 906, the position of core 908 may also be determined using the position of ejector rod 906. Thus, a plurality of measurements taken at a certain cross section of core 908 by multiple ultrasonic measurement unit assemblies may be associated. In certain embodiments having both compressional and shear ultrasonic wave transmitters and receivers, the compressional and shear ultrasonic wave data for a certain cross section of core 908 may be associated. Received ultrasonic wave data for a plurality of cross sections of core 908 may be compiled to create a wave profile for core 908.

Figure 7:
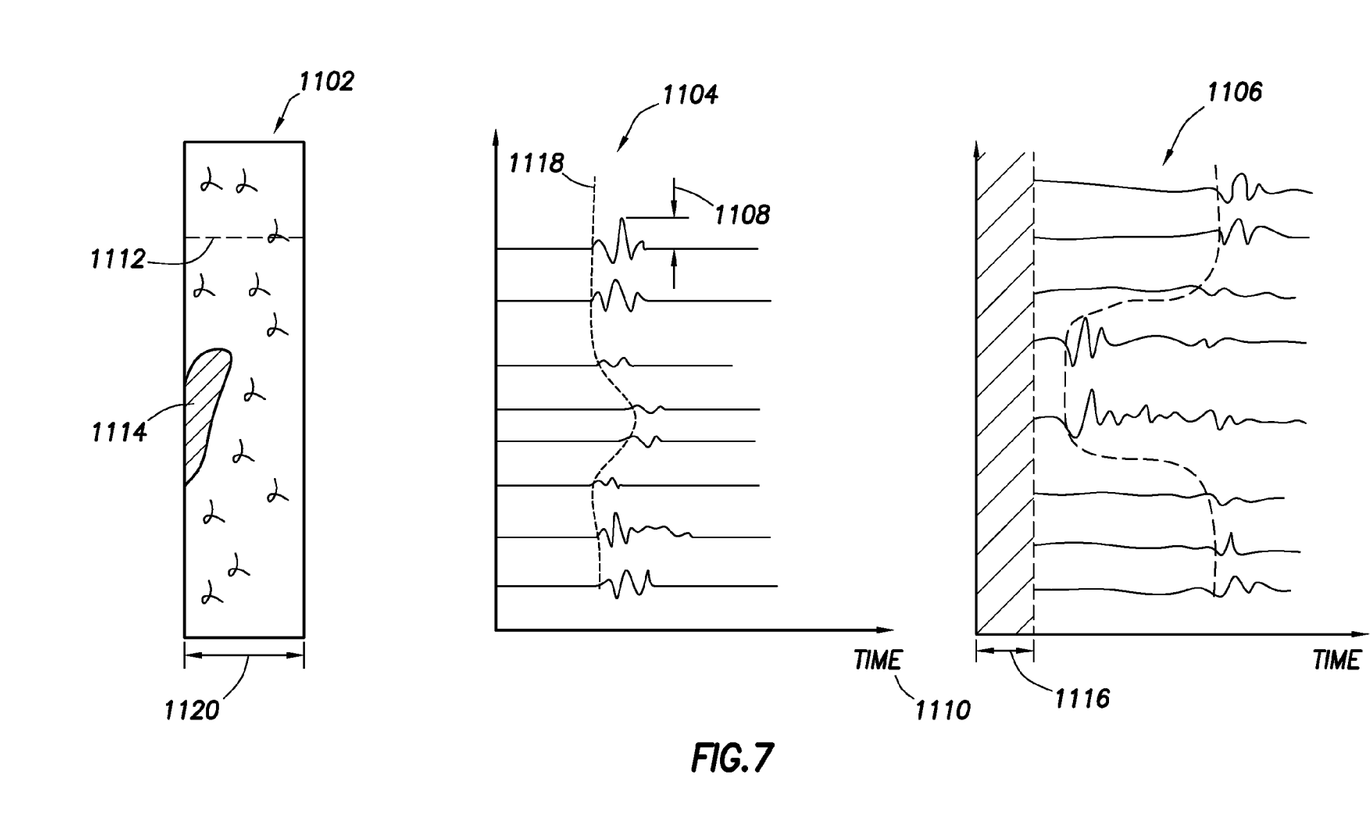
FIG. 7 shows a cross section of an exemplary core and two exemplary graphs in accordance with one or more embodiments of the present disclosure.

Referring to FIG. 7, an exemplary core 1102, a first compressional ultrasonic wave profile 1104 collected by a first ultrasonic measurement unit assembly configured as a receiver (not shown), and a second compressional ultrasonic wave profile 1106 collected by a second ultrasonic measurement unit assembly (not shown) configured to both transmit and receive ultrasonic waves are shown. First and second compressional ultrasonic wave profiles 1104, 1106 may be graphed showing wave amplitude 1108 as a function of time 1110 for a plurality of cross sections 1112 of core 1102. Additionally, time 1110 and amplitude 1108 may be used together to trace a wave arrival time profile 1118. Using wave arrival time profile 1118, a compressional wave speed, or inversely, a compressional wave slowness, may be calculated using a diameter 1120 of core 1102. In certain embodiments, calibration data such as, for example, propagation delays caused by cover plates 1015 (FIG. 6), may be used in calculating the compressional wave speed. Similarly, shear wave speed, or inversely, shear wave slowness, may be generated using a shear wave arrival profile, core diameter 1120, and calibration data. Those of ordinary skill in the art will appreciate that shear ultrasonic wave profiles, and a combination of compression and shear ultrasonic wave profiles may also be created.

Looking to core 1102 and first compressional ultrasonic wave profile 1104 obtained using a receiver positioned diametrically opposite a transmitter, it can be seen that the presence of a vug 1114 in core 1102 may be detected by delayed and/or attenuated ultrasonic wave arrivals at the first ultrasonic measurement unit assembly. Looking to second compressional ultrasonic wave profile 1106, an initial time period, or firing period 1116, during which the second ultrasonic measurement unit assembly transmits ultrasonic waves is excluded from analysis, and only reflected ultrasonic waves received by the second ultrasonic measurement unit assembly are shown. It can be seen that the presence of vug 1114 may also be detected by early ultrasonic wave arrivals at the second ultrasonic measurement unit assembly having large amplitudes 1108. In certain embodiments, vug 1114 may include a cavity, void, or large pore in a rock that may be lined with mineral precipitates. Similarly, the presence of other fractures and defects may also be detected by analyzing arrival times and amplitudes of ultrasonic waves in addition to polarity switches of ultrasonic wave oscillations. A homogenous core may exhibit an approximately constant ultrasonic wave profile 1104, 1106 over a significant portion of core length. Thus, homogeneity of core 1102 may be determined while core 1102 is downhole. Integrity of core 1102 may be determined after homogeneity of core 1102 is determined. A core 1102 found to include a large vug or fracture may be determined to lack structural integrity. In certain embodiments, further analysis of core 1102 may take place once core 1102 has been retrieved, and thus, a sufficient volume of formation may be required.

In addition to homogeneity and integrity of core 1102, the lithology of core 1102 may be determined. A representative value of the compressional wave speed or the shear wave speed may be selected and may be compared to values of compressional or shear wave speeds obtained in known formations such as, for example, sandstone, shale, limestone, dolomite, salt, etc. A representative value of the compressional or shear wave speed may be chosen from a homogeneous portion of core 1102. Those of ordinary skill in the art will appreciate that other representative values may be obtained such as, for example, a representative value of a compressional speed to shear speed ratio or representative values of slowness. In select embodiments, determining a lithology of core 1102 may be useful in verifying whether or not a core has been extracted from an inclusion such as, for example, a shale lens, that is not representative of a reservoir formation such as, for example, sandstone. In one or more embodiments, a core captured from an inclusion may not provide information from which characteristics of the reservoir formation may be drawn.

In certain embodiments, a length of core 1102 may be measured by determining when a bottom end of core 1102 reaches a top pair of ultrasonic measurement unit assemblies by detecting at what point ultrasonic waves sent by a transmitter transition from a signature indicative of wellbore fluid to a signature indicative of a formation rock. The position of the ejection rod may be measured when a bottom end of the ejection rod, and thus, a top end of core 1102, reach the top pair of ultrasonic measurement unit assemblies. The difference between the two ejector rod locations may provide an estimate of the length of core 1102. Additionally, the absence of a core 1102 may also be detected.

Analysis of the homogeneity, integrity, and lithology of a core may determine a quality of the core. For example, a core showing relatively high homogeneity and integrity, and having a desired lithology, may be a high quality core. Conversely, a core having relatively little homogeneity and integrity, and having an undesired lithology, may be a low quality core. Those of ordinary skill in the art will appreciate that factors considered in determining a high or low quality core may include, for example, homogeneity, integrity, and/or lithology.

Analysis of homogeneity, integrity, and lithology of a core may occur in real time, if desired, as ultrasonic measurement unit assemblies relay collected data to a surface display unit. An operator may determine the quality of the core in real time as collected data is displayed on the surface display unit. If a first core is determined to be a low quality core, sidewall coring tool 802 (FIGS. 4A and 4B) may be rotated around the wellbore longitudinal axis, or translated along the wellbore longitudinal axis to extract a second core from formation 834 (FIGS. 4A and 4B) at the same depth or in the same formation from which the first core was extracted. The rotation of sidewall coring tool 802, the translation of sidewall coring tool 802 and the extraction of an additional core from formation 834 may be repeated until a core having high quality, or sufficient quality, is obtained, or until the coring operation is aborted. Once a high quality core is obtained, sidewall coring tool 802 may be lowered or raised within borehole 812 to collect additional core samples at different depths. In certain embodiments, as discussed above, core quality may be determined while sidewall coring tool 802 is still in wellbore 812. Thus, a yield of representative cores captured during a single run of the coring tool may be increased, thereby reducing the need of a costly additional run that may otherwise be needed to collect sufficient information about formation 834 traversed by wellbore 812.

Referring back to FIG. 6, insulating body 1006 may be sealed using electrical insulation such as, for example, an o-ring seal 1017 and cover plate 1015. Cover plate 1015 may be fitted into an inner portion 1019 of insulating body 1006 and may be secured using o-ring seal 1017 between inner portion 1019 and cover plate 1015, thereby encapsulating piezoelectric ceramic 1012. Insulating body 1006 of ultrasonic measurement unit assembly 912 may be formed from an insulating material to provide electrical insulation. In certain embodiments, the insulating material may be formed from a material such as, for example, polytetrafluoroethylene (PTFE), polyether-etherketone (PEEK), or polyether-ketone (PEK); however, those of ordinary skill in the art will appreciate that other insulating materials may be used. Further, an inside of insulating body 1006 may be filled with hydraulic oil, silicone gel, or other fluids to hydraulically insulate ultrasonic measurement unit assembly 912 to provide resistance to high downhole pressures.

Ultrasonic measurement unit assemblies 912 may be configured to receive ultrasonic waves to be relayed or stored; however, the receivers may also receive and transmit undesired acoustic signals, or "noise". As such, in certain embodiments, attenuator devices (not shown) may additionally be disposed in tool body 902 (FIG. 5) to prevent propagation of acoustic waves through the tool and to reduce noise. To further reduce noise, insulating body 1006 may also house a acoustically damping layer 1008 which may be formed from a composite material suitable for providing acoustic wave impedance such as, for example, tungsten-loaded rubber.

Referring back to FIGS. 4A and 4B, after core 823 is analyzed in core analysis section 828, an ejector rod 906 (FIG. 5) may force core 823 into core storage section 830. In certain embodiments, core storage section 830 may be configured to store up to approximately 25 cores, although it should be understood that fewer or additional cores may be accommodated.

Embodiments disclosed herein may provide for one or more of the following advantages. A tool and method in accordance with the present disclosure may be included within one or more of the embodiments shown in FIGS. 1-4B, in addition to being included within other tools and/or devices that may be disposed downhole within a formation. Further, a tool and a method in accordance with one or more embodiments of the present disclosure may provide for obtaining and analyzing a first formation sample. The first formation sample taken at a first depth may be analyzed using ultrasonic measurement unit assemblies which may send data characterizing first formation sample to a surface display unit in real time. Operators may construct an ultrasonic wave profile and may determine a quality of the formation sample based on the analysis and the ultrasonic wave profile. If it is determined that a low quality sample has been extracted and analyzed, operators may choose to extract a second formation sample at the first depth. However, if it is determined that a high quality sample has been extracted, operators may decide to take a second formation sample a height different from the first height.

Embodiments disclosed herein may advantageously provide for multiple formation samples to be extracted and analyzed without removing a sidewall coring tool from a borehole. The extracted samples may be analyzed while downhole to determine if the sample is acceptable. Thus, an apparatus and method in accordance with the present disclosure may decrease sidewall coring tool trips into and out of a borehole. As such, embodiments disclosed herein may provide significant time and cost savings. Additionally, because each formation sample may be analyzed downhole to determine its quality, multiple samples may be collected at a particular depth until a high quality sample is obtained or until the core operation is aborted.

In one aspect, embodiments disclosed herein relate to a core analysis unit for use in a coring tool, the core analysis unit including a passageway extending axially through the core analysis unit, wherein the passageway is configured to receive a core, an ejector rod configured to push the core through the passageway, a plurality of cavities disposed on an inner surface of the passageway, wherein the plurality of cavities are positioned in diametrically opposed pairs, and a plurality of ultrasonic measurement unit assemblies disposed in the plurality of cavities such that at least two of the ultrasonic measurement unit assemblies are positioned in diametrically opposed pairs across the passageway.

In yet another aspect, embodiments disclosed herein relate to a method for obtaining and analyzing a formation sample, the method including extracting a first core from a sidewall of a wellbore with a coring tool at a first depth, ultrasonically measuring a sound speed of the first core, transmitting the ultrasonically measured sound speed of the first core to a surface display unit, analyzing the ultrasonically measured sound speed in real time, determining the quality of the first core, extracting a second core at the first depth if the first core is determined to be low quality; and extracting the second core at a second depth if the core first is determined to be high quality.

The present disclosure introduces an apparatus comprising: a downhole core analysis unit comprising: an axially extending passageway configured to receive a core removed from a sidewall of a borehole extending into a subterranean formation; an ejector rod configured to push the core through the passageway; a plurality of cavities disposed on an inner surface of the passageway, wherein the plurality of cavities are positioned in diametrically opposed pairs; and a plurality of ultrasonic measurement unit assemblies disposed in the plurality of cavities such that at least two of the ultrasonic measurement unit assemblies are positioned in diametrically opposed pairs across the passageway. Each ultrasonic measurement unit assembly may comprise: at least one insulating body; a damping layer and a piezoelectric ceramic disposed within the insulated body; and a cover plate configured to seal the damping layer and the piezoelectric ceramic inside the insulated body. The cover plate may substantially comprise aluminum. The apparatus may further comprise a compressible coupling disposed between an outer surface of at least one insulating body and a back surface of a cavity. The piezoelectric ceramic may be polarized in a radial direction and configured to measure a compressional sound speed across the core. The piezoelectric ceramic may also or alternatively be polarized in an axial direction and configured to measure a shear sound speed across the core. The apparatus may further comprise a position measurement unit configured to determine a position of the ejector rod with respect to the passageway. The apparatus may further comprising a telemetry system coupled to at least one ultrasonic measurement unit assembly and configured to transmit data from the at least one ultrasonic measurement unit assembly and the ejector rod to a surface display unit.

The present disclosure also introduces an apparatus comprising: a downhole tool, comprising: a coring bit configured to extract a core from a sidewall of a wellbore extending into a subterranean formation; a core analysis unit configured to obtain a sound speed measurement for the core; a core storage unit configured to store the core; and a telemetry package configured to transmit the sound speed measurement to a surface unit. The core analysis unit may further comprise: a body having an axially extending passageway configured to receive the core; an ejector rod configured to push the core through the passageway; a plurality of cavities disposed on an inner surface of the body in diametrically opposed pairs; and a plurality of ultrasonic measurement unit assemblies disposed in the plurality of cavities such that at least two of the ultrasonic measurement unit assemblies are positioned in a diametrically opposed pair. Each ultrasonic measurement unit assembly may comprise: an insulating body; a damping layer and a piezoelectric ceramic disposed within the insulated body; and a cover plate configured to seal the damping layer and the piezoelectric ceramic inside the insulated body.

The present disclosure also introduces a method comprising: extracting a first core from a sidewall of a wellbore with a coring tool at a first depth; ultrasonically measuring a sound speed of the first core; transmitting the ultrasonically measured sound speed of the first core to a surface display unit; analyzing the ultrasonically measured sound speed in real time; extracting a second core at the first depth when the first core is determined to be low quality based on the real-time analysis of the ultrasonically measured sound speed; and extracting the second core at a second depth when the core first is determined to be high quality based on the real-time analysis of the ultrasonically measured sound speed. Ultrasonically measuring the sound speed of the first core may comprise: transmitting compressional ultrasonic waves to the first core; measuring a compressional sound speed of the first core; transmitting shear ultrasonic waves to the first core; and measuring a shear sound speed of the first core. A first ultrasonic measurement unit may transmit the ultrasonic wave to the first core and a second ultrasonic measurement unit may receive the transmitted ultrasonic wave. The first ultrasonic measurement unit may be disposed on a first side of the first core and the second ultrasonic measurement unit may be disposed diametrically opposite the first ultrasonic measurement unit. A first ultrasonic measurement unit may transmit the ultrasonic wave to the first core and the first ultrasonic measurement unit may receive the transmitted ultrasonic wave. The method may further comprise: measuring a position of the first core with respect to the at least one ultrasonic measurement unit; indexing the sound speed measurements and the position of the first core; and creating an ultrasonic wave profile of the first core. The method may further comprise determining at least one of homogeneity, integrity, and lithology of the first core based on the created ultrasonic wave profile. The method may further comprise: measuring a first position of the first core, wherein at the first position a bottom end of the core contacts a first ultrasonic measurement unit; measuring a second position of the first core, wherein at the second position a top end of the core contacts the first ultrasonic measurement unit; and determining a length of the first core by determining a difference between the first position of the first core and the second position of the first core. Ultrasonically measuring the sound speed of the first core may comprise measuring an arrival time of an ultrasonic signal.

The foregoing outlines feature several embodiments so that those skilled in the art may better understand the aspects of the present disclosure. Those skilled in the art should appreciate that they may readily use the present disclosure as a basis for designing or modifying other processes and structures for carrying out the same purposes and/or achieving the same advantages of the embodiments introduced herein. Those skilled in the art should also realize that such equivalent constructions do not depart from the spirit and scope of the present disclosure, and that they may make various changes, substitutions and alterations herein without departing from the spirit and scope of the present disclosure.

The Abstract at the end of this disclosure is provided to comply with 37 C.F.R. §1.72(b) to allow the reader to quickly ascertain the nature of the technical disclosure. It is submitted with the understanding that it will not be used to interpret or limit the scope or meaning of the claims.

What is claimed is:

1. An apparatus, comprising:
    a downhole core analysis unit comprising:
        an axially extending passageway configured to receive a core removed from a sidewall of a borehole extending into a subterranean formation;
        an ejector rod configured to push the core through the passageway;
        a plurality of cavities disposed on an inner surface of the passageway; and
        a plurality of ultrasonic measurement unit assemblies disposed in the plurality of cavities such that at least two of the ultrasonic measurement unit assemblies are positioned in diametrically opposed pairs across the passageway and are radially compressed by axial movement of the core through the passageway.

2. The apparatus of claim 1 wherein each ultrasonic measurement unit assembly comprises:
    at least one insulating body;
    a damping layer and a piezoelectric ceramic disposed within the insulated body; and
    a cover plate configured to seal the damping layer and the piezoelectric ceramic inside the insulated body.

3. The apparatus of claim 2 wherein the cover plate substantially comprises aluminum.

4. The apparatus of claim 2 further comprising a compressible Coupling disposed between an outer surface of the at least one insulating body and a back surface of a cavity of the plurality of cavities.

5. The apparatus of claim 2 wherein the piezoelectric ceramic is polarized in a radial direction and configured to measure a compressional sound speed across the core.

6. The apparatus of claim 2 wherein the piezoelectric ceramic is polarized in an axial direction and configured to measure a shear sound speed across the core.

7. The apparatus of claim 1 further comprising a position measurement unit configured to determine a position of the ejector rod with respect to the passageway.

8. The apparatus of claim 1 further comprising a telemetry system coupled to at least one ultrasonic measurement unit assembly of the plurality of ultrasonic measurement assemblies and configured to transmit data from the at least one ultrasonic measurement unit assembly and the ejector rod to a surface display unit.

9. The apparatus of claim 1 comprising:
    a coring bit configured to extract the core from the sidewall; and
    a core storage unit configured to store the core.

10. The apparatus of claim 1 comprising a telemetry package configured to transmit a sound speed measurement generated by the core analysis unit to a surface unit.

11. A method comprising:
    pushing, via an ejector rod, a first core through an axially extending passageway of a downhole core analysis unit; and
    transmitting ultrasonic waves between a plurality of ultrasonic measurement unit assemblies to obtain a measurement—for the first core, wherein the plurality of ultrasonic measurement unit assemblies are disposed in a plurality of cavities disposed on an inner surface of the passageway such that at least two of the ultrasonic measurement unit assemblies are positioned in diametrically opposed pairs across the passageway and are radially compressed by axial movement of the first core through the passageway.

12. The method of claim 11 comprising:
   extracting the first core from a sidewall of a wellbore with a coring tool at a first depth; and
   extracting a second core at the first depth in response to determining that the first core is low quality based on real-time analysis of sound speed.

13. The method of claim 11 comprising:
   extracting the first core from a sidewall of a wellbore with a coring tool at a first depth; and
   extracting a second core at a second depth in response to determining that the first core is high quality based on real-time analysis of sound speed.

14. The method of claim 11 wherein transmitting ultrasonic waves comprises:
   transmitting compressional ultrasonic waves to the first core;
   measuring a compressional sound speed of the first core;
   transmitting shear ultrasonic waves to the first core; and
   measuring a shear sound speed of the first core.

15. The method of claim 11 wherein transmitting ultrasonic waves comprises:
   transmitting a first ultrasonic wave from a first ultrasonic measurement unit to the first core; and
   receiving the first ultrasonic wave at a second ultrasonic measurement unit.

16. The method of claim 11 comprising:
   measuring a position of the first core with respect to at least one ultrasonic measurement unit of the plurality of ultrasonic measurement unit assemblies; and
   indexing received ultrasonic waves with the position of the first core to compile an ultrasonic wave profile of the first core.

17. The method of claim 16 comprising determining at least one of homogeneity, integrity, and lithology of the first core based on the created ultrasonic wave profile.

18. The method of claim 11 comprising:
   measuring a first position of the first core, wherein at the first position a bottom end of the first core contacts a first ultrasonic measurement unit of the plurality of ultrasonic measurement unit assemblies;
   measuring a second position of the first core, wherein at the second position a top end of the core contacts the first ultrasonic measurement unit; and
   determining a length of the first core by determining a difference between the first position of the first core and the second position of the first core.

19. The method of claim 11 wherein the measurement comprises a sound speed and further comprising measuring an arrival time of the ultrasonic waves to determine the sound speed for the first core.

* * * * *